United States Patent [19]

Scollo-Lavizzari

[11] Patent Number: 5,244,900
[45] Date of Patent: Sep. 14, 1993

[54] METHOD OF USE AND COMPOSITIONS

[75] Inventor: Giuseppe Scollo-Lavizzari, Basel, Switzerland

[73] Assignee: Hoffmann-La Roche Inc., Nutley, N.J.

[21] Appl. No.: 811,000

[22] Filed: Dec. 20, 1991

Related U.S. Application Data

[63] Continuation of Ser. No. 518,584, May 1, 1990, abandoned.

[30] Foreign Application Priority Data

May 19, 1989 [CH] Switzerland .......................... 1886/89

[51] Int. Cl.$^5$ ............................................ A61K 31/55
[52] U.S. Cl. ..................................................... 514/220
[58] Field of Search ......................................... 514/220

[56] References Cited

U.S. PATENT DOCUMENTS

| | | | |
|---|---|---|---|
| 4,316,839 | 2/1982 | Gerecke et al. | 540/498 |
| 4,346,031 | 8/1982 | Gerecke et al. | 514/210 |
| 4,346,032 | 8/1982 | Gerecke et al. | 514/823 |
| 4,346,034 | 8/1982 | Gerecke et al. | 514/210 |
| 4,346,035 | 8/1982 | Gerecke et al. | 514/210 |
| 4,346,036 | 8/1982 | Gerecke et al. | 514/210 |
| 4,352,815 | 10/1982 | Hunkeler et al. | 514/210 |
| 4,352,816 | 10/1982 | Hunkeler et al. | 514/210 |
| 4,352,817 | 10/1982 | Hunkeler et al. | 514/210 |
| 4,352,818 | 10/1982 | Hunkeler et al. | 514/210 |
| 4,353,827 | 10/1982 | Hunkeler et al. | 514/210 |
| 4,359,420 | 11/1982 | Gerecke et al. | 514/210 |
| 4,362,732 | 12/1982 | Hunkeler et al. | 514/210 |
| 4,489,003 | 12/1984 | Hunkeler et al. | 514/210 |
| 4,775,671 | 10/1988 | Hunkeler et al. | 514/210 |
| 4,863,920 | 9/1989 | Hunkeler et al. | 514/210 |

FOREIGN PATENT DOCUMENTS

| | | |
|---|---|---|
| 71583/87 | 10/1987 | Australia . |
| 0027214 | 4/1981 | European Pat. Off. . |
| 0059387 | 9/1982 | European Pat. Off. . |
| 0100906 | 2/1984 | European Pat. Off. . |
| 109921 | 5/1984 | European Pat. Off. . |
| 0285837 | 10/1988 | European Pat. Off. . |
| 395527 | 10/1990 | European Pat. Off. . |
| 0059390 | 9/1992 | European Pat. Off. . |
| 2093842 | 9/1982 | United Kingdom . |

OTHER PUBLICATIONS

Methods Find. Exp. Clin. Pharmacol., vol. 9, pp. 341-347 (1987).
Eur. Neurol., vol. 22, pp. 7-11 (1983).
Drug Dev. Res., vol. 14, pp. 359-362 (1988).
Ars. Med., vol. 78, pp. 536-541 (1988).
Neuropharmacol., vol. 24, pp. 957-963 (1985).

Forster, et al., Effects of a Specific Benzodiazepin Antagonist (Ro 15-1788) on Cerebral Blood Flow, Anesth. Analg. vol. 66, pp. 309-313 (1987).
Hoffman, W. E. et al., Cerebrovascular and Cerebral Metabolic Effects of Flurazepam and A Benzodiazepine Antagonist, 3-Hydroxymethyl-B-carbine, Eur. J. of Pharmacology, vol. 106, pp. 585-591 (1984).

Primary Examiner—S. J. Friedman
Attorney, Agent, or Firm—George M. Gould; George W. Johnston; Ellen Ciambrone Coletti

[57] ABSTRACT

A compound of the formula

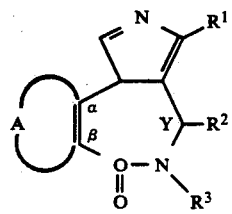

I wherein A together with the two carbon atoms denoted by α and β is the group

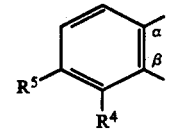

(a)

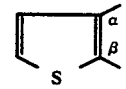

(b)

or

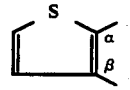

(c)

and further wherein the substituents $R^1$, $R^2$, and $R^3$ are as described in the specification, can be used in the treatment of neurological symptoms which are associated with circulatory disorders of the brain, especially in the treatment of neurological symptoms which are associated with cerebrovascular seizures.

6 Claims, No Drawings

METHOD OF USE AND COMPOSITIONS

This is a continuation of application Ser. No. 07/518,584 filed May 1, 1990, now abandoned.

BRIEF SUMMARY OF THE INVENTION

The invention relates to the use of compounds of the formula

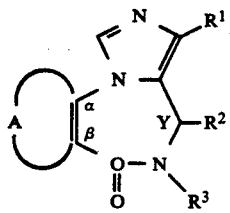

wherein A together with the two carbon atoms denoted by $\alpha$ and $\beta$ is the group

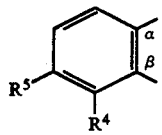

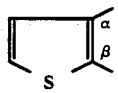

or

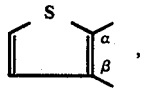

$R^1$ is halogen, cyano, lower alkyl, lower 1-alkenyl, lower alkoxymethyl or the group —COOR$^6$ or —C≡C—R$^7$, $R^2$ is hydrogen and $R^3$ is lower alkyl or $R^2$ and $R^3$ taken together are dimethylene or trimethylene, $R^4$ and $R^5$ each is hydrogen, halogen, trifluoromethyl or lower alkyl, $R^6$ is lower alkyl, $C_{3-7}$-cyclo-alkyl or $C_{3-7}$-cycloalkyl-lower alkyl and $R^7$ is hydrogen, lower alkyl, lower hydroxyalkyl, lower alkoxyalkyl, $C_{3-7}$-cycloalkyl-lower alkyl, $C_{3-7}$-cycloalkyl-lower hydroxyalkyl, $C_{3-7}$-cycloalkyl-lower alkoxyalkyl, ($C_{3-7}$-cycloalkyl-lower alkoxy)-lower alkyl, (aryl-lower alkoxy)-lower alkyl, lower alkanoyloxy-lower alkyl, ($C_{3-7}$-cycloalkyl-lower alkanoyloxy)-lower alkyl, $C_{3-7}$-cycloalkylcarbonyloxy-lower alkyl, (aryl-lower alkanoyloxy)-lower alkyl, arylcarbonyloxy-lower alkyl, lower alkenyl, lower hydroxyalkenyl, lower alkoxy-lower alkenyl, ($C_{3-7}$-cycloalkyl-lower alkoxy)-lower alkenyl, (aryl-lower alkoxy)-lower alkenyl, lower alkanoyloxy-lower alkenyl, ($C_{3-7}$-cycloalkyl-lower alkanoyloxy)-lower alkenyl, $C_{3-7}$-cycloalkylcarbonyloxy-lower alkenyl, (aryl-lower alkanoyloxy)-lower alkenyl, arylcarbonyloxy-lower alkenyl, $C_{3-7}$-cycloalkyl, hydroxy-$C_{4-7}$-cycloalkyl or lower alkoxy-$C_{4-7}$-cycloalkyl, and the compounds of formula I having the (S)- or (R,S)-configuration in relation to the carbon atom denoted by $\gamma$ when $R^2$ and $R^3$ taken together are dimethylene or trimethylene, in the treatment of neurological symptoms or complications which are associated with circulatory disorders of the brain, especially in the treatment of neurological symptoms which are associated with cerebrovascular seizures.

The invention relates to the use of compounds of the formula

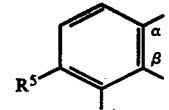

wherein A together with the two carbon atoms denoted by $\alpha$ and $\beta$ is. the group

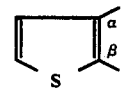

or

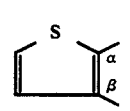

$R^1$ is halogen, cyano, lower alkyl, lower 1-alkenyl, lower alkoxymethyl or the group —COOR$^6$ or —C≡C—R$^7$, $R^2$ is hydrogen and $R^3$ is lower alkyl or $R^2$ and $R^3$ taken together are dimethylene or trimethylene, $R^4$ and $R^5$ each is hydrogen, halogen, trifluoromethyl or lower alkyl, $R^6$ is lower alkyl, $C_{3-7}$-cyclo-alkyl or $C_{3-7}$-cycloalkyl-lower alkyl and $R^7$ is hydrogen, lower alkyl, lower hydroxyalkyl, lower alkoxyalkyl. $C_{3-7}$-cycloalkyl-lower alkyl. $C_{3-7}$-cycloalkyl-lower hydroxyalkyl, $C_{3-7}$-cycloalkyl-lower alkoxyalkyl, ($C_{3-7}$-cycloalkyl-lower alkoxy)-lower alkyl, (aryl-lower alkoxy)-lower alkyl, alkanoyloxy-lower alkyl, ($C_{3-7}$-cycloalkyl-lower alkanoyloxy)-lower alkyl, $C_{3-7}$-cycloalkylcarbonyloxy-lower alkyl, (aryl-lower alkanoyloxy)-lower alkyl, arylcarbonyloxy-lower alkyl, lower alkenyl lower hydroxyalkenyl, lower alkoxy-lower alkenyl, ($C_{3-7}$-cycloalkyl-lower alkoxy)-lower alkenyl, (aryl-lower alkoxy)-lower alkenyl, lower alkanoyloxy-lower alkenyl, ($C_{3-7}$-cycloalkyl-lower alkanoyloxy)-lower alkenyl, $C_{3-7}$-cycloalkylcarbonyloxy-lower alkenyl, (aryl-lower alkanoyloxy)-lower alkenyl arylcarbonyloxy-lower alkenyl, $C_{3-7}$-cycloalkyl, hydroxy-$C_{4-7}$-cycloalkyl or lower alkoxy-$C_{4-7}$-cycloalkyl, and the compounds of formula I having the (S)- or (R,S)-configuration in relation to the carbon atom denoted by $\gamma$ when $R^2$ and $R^3$ taken together are dimethylene or trimethylene, in the treatment of neurological symptoms or complications which are associated with circulatory disorders of the brain, especially in the treatment of neurological symptoms which are associated with cerebrovascular seizures Objects of the invention include the use of the compounds of formula I in the treatment of neurological symptoms or complications which are associated with circulatory disorders of the brain, the use of the compounds of formula I above for the preparation of corresponding medicaments as well as a method and medicaments for the treatment of the mentioned neurological symptoms and complications.

As used herein, the term "lower" denotes residues and compounds having 1 to 7, preferably 1 to 4, carbon atoms. The term "alkyl" denotes a straight-chain or branched saturated hydrocarbon residues, for example, methyl, ethyl, n-propyl, isopropyl, n-butyl, isobutyl, s-butyl, t-butyl and the like. The term "alkoxy" denotes an alkyl residue, as previously described, which is attached via an oxygen atom. The term "cyclo-alkyl" denotes a cyclic, saturated hydrocarbon residue, such as, cyclopropyl, cyclobutyl, cyclopentyl and cyclohexyl. The term "alkanoyloxy" denotes a residue derived from a straight-chain or branched fatty acid, such as, acetoxy, ethoxy, butoxy and the like. The term "alkenyl" denotes a straight-chain or branched hydrocarbon residue which contains at least one olefinic double bond, such as, cis- and trans-2-buten-2-yl and 1-buten-3-yl. The term "aryl" preferably denotes a mono-cyclic aromatic hydrocarbon residue which is preferably unsubstituted or substituted by lower alkyl, lower alkoxy and/or halogen. The term "halogen" denotes fluorine, chlorine, bromine or iodine.

The compounds of formula I are known substances, their preparation and their known benzodiazepine-antagonistic properties are described, for example, in European Patent Publications No. 27 214; 59 387; 59 389; 59 390; 100 906; and 285 837.

In, the scope of the invention flumazenil, ethyl 8-fluoro-5,6-dihydro-5-methyl-6-oxo-4H-imidazo[1,5-a][1,4]benzodiazepine-3-carboxylate, is preferably the compound of formula I.

By virtue of the benzodiazepine-antagonistic properties, the compounds of formula I are capable of specifically blocking, by competitive inhibition, the central effects of preparations which display their activity via benzodiazepine receptors. The compounds of formula I can therefore be used to nullify the central damping activities of benzodiazepines. In anaesthesia, the compounds of formula I can be used, for example, to terminate narcosis which has been initiated and maintained by benzodiazepines in in-patients. In intensive care they can be used, for example, to nullify the central effects of benzodiazepines in a case of drug overdosage and thereby restore spontaneous respiration and consciousness.

It has now surprisingly been found that the compounds of formula I are also effective in the treatment of neurological symptoms or complications which are associated with circulatory disorders of the brain, that is, have no connection with the administration or intake of benzodiazepines.

Circulatory disorders of the brain, as occur, for example, in cerebrovascular seizures, are characterized by a focal symptomatology which appears suddenly or subacutely. Typical neurological symptoms are paralyses, sensitiveness disorders, consciousness disorders, speech disorders and other communication disorders.

In accordance with the invention, the compounds of formula I can be used to treat neurological symptoms or complications after circulatory disorders of the brain, including the above-mentioned. For example, the consciousness of stuporous or comatose patients after a cerebrovascular seizure can be restored. After treatment with a compound of formula I, the patients are as a rule immediately responsive and react to simple requests. This finding is in accord with the electroencephalograms taken and the motor activities of the hands measured and quantified periodically by means of piezoelectric sensors (actigraphs).

In the case of hemiplegic patients, a significant remission of the paresis could be observed after treatment with a compound of formula I.

At the present time, no medicaments are available to treat neurological symptoms or complications in patients having circulatory disorders of the brain. The possibility provided by the compounds of formula I above to treat such symptoms and complications obviously offers great benefits in diagnosis, therapy and rehabilitation. The nullifying of consciousness disorders is, for example, decisive for prognosis. The development of lasting neurological disorders can be prevented or at least strongly inhibited at an early stage. Rehabilitation is facilitated and any physiotherapeutic measures can begin earlier. These possibilities, which are provided by the use in accordance with the invention of compounds of formula I above, must substantially improve the prospects of curing the patient.

The action in accordance with the invention of the compounds of formula I can be demonstrated on the basis of the cases described hereinafter in which flumazenil was used as the representative member of the class of compound defined by formula I.

Patients Nos. 1–3, who were admitted were hospitalized with symptoms and indication of a cerebrovascular seizure associated with consciousness disorders. All three patients had taken no benzodiazepines, confirmed during the study by a negative result in the benzodiazepine screening. The patients were in a stable haemodynamic and respiratory condition, without electrolyte abnormality or other causes for the neurological symptoms.

A complete neurological investigation was carried out prior to the administration of flumazenil and for two hours thereafter. The haemodynamic and respiratory functions were also monitored and two patients were monitored electroencephalographically. In the case of the third patient, an actigraph was used to measure and quantify the motor activity of the hands.

Patient No. 1

A 72 year old female was admitted with the diagnosis of a cerebrovascular seizure associated with right hemiplegia and stupor. Computer tomography pointed to multiple infarcts without signs of an intercranial bleeding.

After the intravenous administration of 2 mg of flumazenil over a 15 minutes period, the patient responded to simple commands. In the course of the next hour, she again lost consciousness, whereupon she received by injection, an additional 1 mg of flumazenil ,over a 10 minutes period and then again responded to simple commands. The rest-EEG showed asymmetry and practically no $\alpha$-activity. After 10 minutes, the pattern changed to $\alpha$-activity on the right side.

Patient No. 2

A 52 year old male, a regular dialysis patient, was admitted in a comatose condition. The patient was in a deep coma and showed no focal neurological signs. Fundoscopy was normal. Blood analysis showed a metabolic acidosis with a pH of 7.25 with a hypercalemia of 6.2 mval/l.

An emergency dialysis was carried out because of the presumed intake of more than one medicament including benzodiazepines. The condition of the patient had not improved after four hours. The patient then received by injection 1 mg of flumazenil over a period of 10 minutes, whereupon the patient regained full consciousness and denied categorically that he had taken any medicament. Toxicological investigations confirmed this statement; no blood level of barbiturates or benzodiazepines could be detected. Computer-tomographical investigation carried out later indicated cortical and central-generalized atrophy, lacunar infarcts in the right putamen and in the left caudal nucleus and calcium deposits in the space of the tentorum and the pallidum. The patient could be discharged later in a normal neurological condition and without consequences.

Patient No. 3

A 89 year old female appeared with right hemiplegia and stupor. Ten (10) minutes after the administration of 1 mg of flumazenil she awoke and reacted to verbal commands and she also showed some movement of the paralyzed side of her body.

A statistically significant difference between the movements prior to and after the treatment could be established with the actigraph. The patient could be discharged later with complete consciousness and with an insignificant motor infirmity.

Patients Nos. 4 and 5. who were admitted into the study, were also hospitalized with symptoms and indication of a cerebrovascular seizure. Both were hemiplegic, responsive and cooperative. In both patients, the development of the paresis was investigated by measuring the strength of the hands prior to and after treatment with flumazenil.

Patient No. 4

A 42 year old female was hospitalized with the diagnosis of a cerebrovascular seizure in the region of the right external capsule with largely transient left hemisymptomatics and migraine.

The cerebrovascular seizure occurred in complete good health. Previously, the patient had no headaches and no risk factors existed. Eleven (11) days after the hospitalization, strength measurement of the hands gave 7 kg for the right and 3 kg for the left, subsequently, the patient received perorally 10 mg of flumazenil. The strength measurement carried out 10 minutes later gave 7.5 kg for the right and 7 kg for the left. After 20 minutes, the strength was 8 kg for the right and 6 kg for the left. After 30 minutes, the strength 7.8 kg for the right and 6 kg for the left. Treatment with flumazenil brought about a significant increase in the strength of the left and therewith a distinct remission of the paresis.

On the basis of the investigations carried out, a haemodynamic blockage in the region of the cerebral vessels could be excluded. A source of emboli could not be detected there or in the region of the heart. Two days after the treatment with flumazenil, the patient had recovered completely and could be sent home with only still discrete neurological attacks.

Patient No. 5

The patient, a 47 year old female, in completely good health, suddenly felt after standing an acute rotary vertigo as well as an empty feeling in the head. She was no longer able to stand. Somewhat later, hand-accentuated twitching paresthesias occurred in the region of the entire right half of the body and somewhat later also a loss in power of the right hand. For a short time, she also had some difficulty with speech.

After hospitalization, an acute cerebrovascular seizure in the region of the left internal capsule with largely passing sensomotor attacks in the region of the right half of the body was diagnosed. A solitary infarct could be detected. A demyelinizing illness and a vasculitis could be excluded on the basis of the increased findings with a certainty limited by probability. Three days after the hospitalization, the measurement of the strength of the hands gave 8 kg for the left and 5 kg for the right. The patient then received perorally 10 mg of flumazenil. After 15 and 30 minutes, the strength measurement was repeated and on both occasions gave 8 kg for each hand. A short time after the treatment with flumazenil, the patient referred subjectively to a reduction of the paresthesis of the right hand.

The patient could be discharged 5 days later. The motor attacks had disappeared almost completely. The treatment with flumazenil brought about a significant improvement in the strength testing and also a subjective improvement with respect to the sensitiveness disorders (reduction of the paresthesis in the right hand).

In the scope of the invention, the compounds of formula 1 above can be used in the form of perorally, rectally or parenterally administerable pharmaceutical preparations, for example, in the form of tablets, coated tablets, dragees, hard and soft gelatin capsules, suppositories or solutions. The compounds of formula I can also be administered in the form of infusions. Tablets are the preferred dosage form for peroral administration and injection solutions and infusion solutions are preferred dosage forms for intravenous administration.

In the preparation of pharmaceutical dosage forms, the compounds of formula I are processed with pharmaceutically inert, inorganic or organic carriers. Lactose, maize starch or derivatives thereof, talc, stearic acid or its salts and the like can be used, as carriers for tablets, coated tablets, dragees and gelatin capsules Suitable carriers for suppositories are, for example, natural or hardened oils, waxes, fats, semi-solid and liquid polyols and the like. Suitable carriers for the preparation of solutions are, for example, water, polyols, saccharose, invert sugar, glucose and the like.

The pharmaceutical preparations can, moreover, contain preserving agents, solubilizers, stabilizing agents, wetting agents, emulsifying agents, sweetening agents, coloring agents, flavoring agents, salts for varying the osmotic pressure, buffers, coating agents or antioxidants.

As mentioned earlier, the compounds of formula I can be used in the treatment of neurological symptoms which are associated with circulatory disorders of the brain. The dosage can vary depending on the severity of the illness, the age and weight of the patient and will, of course, be adjusted to the individual requirements in each particular case. In general, in peroral administration, a dosage of 5 mg to 50 mg, preferably 10 mg to 30 mg, can be utilized and in intravenous administration a dosage of about 0.5 mg to 5 mg, preferably 1 mg to 3 mg, can be utilized These dosages can also be divided and/or can be administered repeatedly.

The Examples which follow describe illustrative suitable dosage forms utilized in the application of the invention.

EXAMPLE 1

Injection solutions of the following composition are prepared in a known manner:

| | | |
|---|---|---|
| Flumazenil | 0.5 mg | 1 mg |
| Water for injection, containing ethylenediaminetetraacetic acid, acetic acid and sodium chloride as adjuvants | 5 ml | 10 ml |

Infusion solutions can be prepared by diluting the above injection solutions with 0.9 percent sodium chloride, 0.45 percent sodium chloride/2.5 percent dextrose or with 5 percent dextrose for infusion.

EXAMPLE 2

Tablets of the following composition are prepared in an analogous manner:

| | mg/tablet |
|---|---|
| Flumazenil | 10 |
| Lactose | 90 |
| Maize starch | 29 |
| Microcrystalline cellulose | 70 |
| Magnesium stearate | 1 |
| Total | 200 mg |

EXAMPLE 3

Capsules of the following composition are prepared in a known manner:

| | mg/capsule |
|---|---|
| Flumazenil | 10 |
| Lactose | 165 |
| Maize starch | 30 |
| Talc | 5 |
| Total | 210 mg |

I claim:

1. A method of treating neurological symptoms or complications associated with circulatory disorders of the brain that have no connection with the administration or intake of benzodiazepines which comprises administering to a host requiring such treatment an effective amount of a compound of the formula

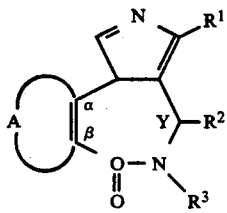

wherein A together with the two carbon atoms denoted by $\alpha$ and $\beta$ is the group

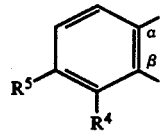

(a)

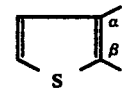

(b)

or

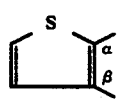

(c)

$R^1$ is halogen, cyano, lower alkyl, lower 1-alkenyl, lower alkoxymethyl or the group —$COOR^6$ or —C≡C—$R^7$, $R^2$ is hydrogen and $R^3$ is lower alkyl or $R^2$ and $R^3$ taken together are dimethylene or trimethylene, $R^4$ and $R^5$ each is hydrogen, halogen, trifluoromethyl or lower alkyl, $R^6$ is lower alkyl, $C_{3-7}$-cyclo-alkyl or $C_{3-7}$-cycloalkyl-lower alkyl and $R^7$ is hydrogen, lower alkyl, lower hydroxyalkyl, lower alkoxyalkyl, $C_{3-7}$-cycloalkyl-lower alkyl, $C_{3-7}$-cycloalkyl-lower hydroxyalkyl, $C_{3-7}$-cycloalkyl-lower alkoxyalkyl, ($C_{3-7}$-cycloalkyl-loweralkoxy)-lower alkyl, (aryl-lower alkoxy)-lower alkyl, lower alkanoyloxy-lower alkyl, ($C_{3-7}$-cycloalkyl-lower alkanoyloxy)-lower alkyl, $C_{3-7}$-cycloalkyl-carbonyloxy-lower alkyl, (aryl-lower alkanoyloxy)-lower alkyl, arylcarbonyloxy-lower alkyl, lower alkenyl, lower hydroxyalkenyl, lower alkoxy-lower alkenyl, ($C_{3-7}$-cycloalkyl-lower alkoxy)-lower alkenyl, (aryl-lower alkoxy)-lower alkenyl, lower alkanoyloxy-lower alkenyl, ($C_{3-7}$-cycloalkyl-lower alkanoyloxy)-lower alkenyl, $C_{3-7}$-cycloalkylcarbonyl-oxy-lower alkenyl, (aryl-lower alkanoyloxy)-lower alkenyl, arylcarbonyloxy-lower alkenyl, $C_{3-7}$-cycloalkyl, hydroxy-$C_{4-7}$-cycloalkyl or lower alkoxy-$C_{4-7}$-cycloalkyl, or a compound of formula I having the (S)- or (R,S)-configuration in relation to the carbon atom denoted by $\gamma$ when $R^2$ and $R^3$ taken together are dimethylene or trimethylene.

2. A method in accordance with claim 1, wherein ethyl 8-fluoro-5,6-dihydro-5-methyl-6-oxo-4H-imidazo[1,5-a][1,4]benzodiazepine-3-carboxylate is utilized as the compound of formula I.

3. The method of claim 1, wherein the circulatory disorder of the brain is a cerebrovascular seizure.

4. The method of claim 3, wherein the neurological symptoms or complications are selected from the group consisting of paralyses, sensitiveness disorders, consciousness disorders, speech disorders and communication disorders.

5. The method of claim 3, wherein the compound of formula I is ethyl-8-fluoro-5,6-dihydro-5-methyl-6-oxo-4H-imidazo[1,5-a][1,4]-benzodiazepine-3-carboxylate.

6. The method of claim 4, wherein the compound of formula I is ethyl-8-fluoro-5,6-dihydro-5-methyl-6-oxo-4H-imidazo[1,5-a][1,4]-benzodiazepine-3-carboxylate.

* * * * *